United States Patent [19]

Kigasawa et al.

[11] 4,166,125

[45] Aug. 28, 1979

[54] 2-OXO-PHENYLBUTANOIC ACID DERIVATIVES

[75] Inventors: Kazuo Kigasawa, Kawasaki; Mineharu Hiiragi, Chofu; Haruhide Ishimaru, Tokyo; Seiji Haga, Yokohama; Keiko Shirayama, Tokyo, all of Japan

[73] Assignee: Grelan Pharmaceutical Co., Ltd., Tokyo, Japan

[21] Appl. No.: 862,206

[22] Filed: Dec. 19, 1977

[30] Foreign Application Priority Data

Apr. 5, 1977 [JP] Japan .................................. 52-38071
Jun. 11, 1977 [JP] Japan .................................. 52-68407
Jun. 22, 1977 [JP] Japan .................................. 52-73369
Nov. 15, 1977 [JP] Japan .................................. 52-136254

[51] Int. Cl.$^2$ ..................... A61K 31/40; C07D 209/46
[52] U.S. Cl. ............................... 424/274; 260/325 PH
[58] Field of Search .................. 260/325 PH; 424/274

[56] References Cited

U.S. PATENT DOCUMENTS

3,884,674  5/1975  Grybek et al. .......................... 71/96
3,895,032  7/1975  Carney .......................... 260/325 PH

FOREIGN PATENT DOCUMENTS

7115288  5/1972  Netherlands ...................... 260/325 PH

OTHER PUBLICATIONS

Igarashi et al., J. Org. Chem., vol. 28, pp. 3088–3092 (1963).
Giraldi et al., Chem. Abstracts, vol. 77, Abstract No. 88292v (1972).

*Primary Examiner*—Alton D. Rollins
*Attorney, Agent, or Firm*—Cooper, Dunham, Clark, Griffin & Moran

[57] ABSTRACT

2-Oxo-phenylbutanoic acid derivatives of the general formula (I)

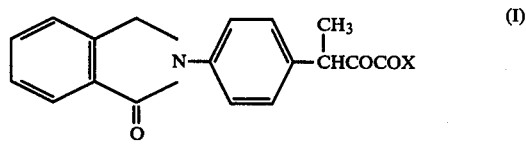

wherein X is amino, hydroxy or lower alkoxy, which have an anti-inflammatory activity and low toxicity, a method for the production of the said derivatives, a pharmaceutical composition containing a therapeutically effective amount of at least one compound of the said derivatives, and the use of such compounds and compositions in therapeutics.

11 Claims, 1 Drawing Figure

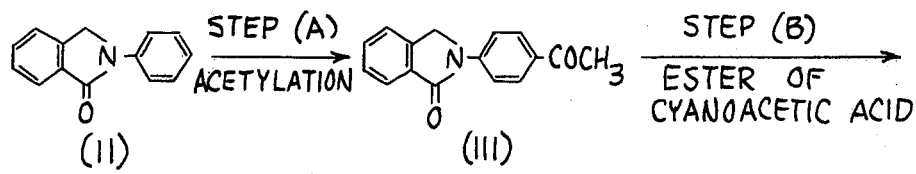
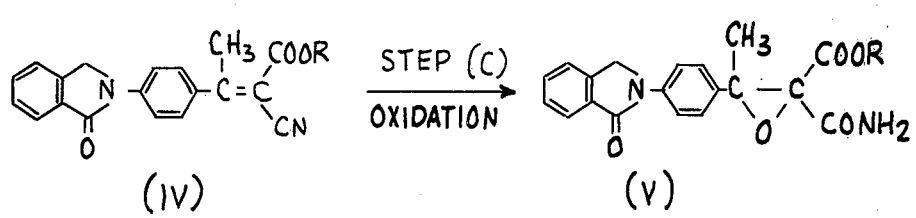
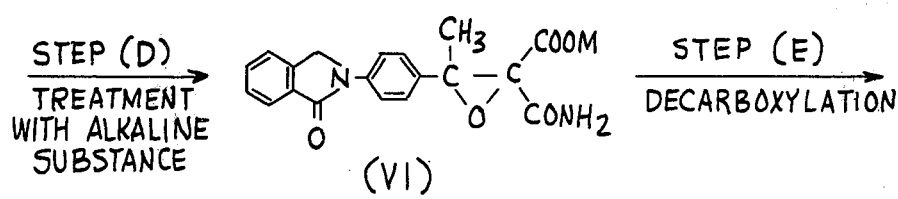
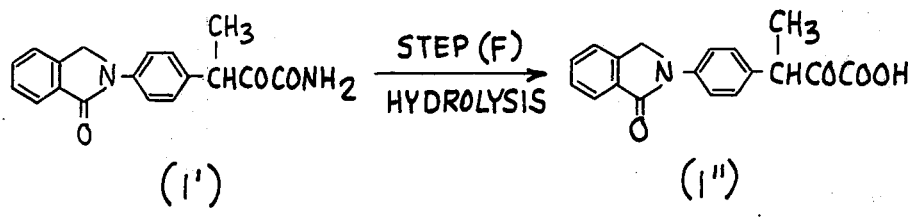
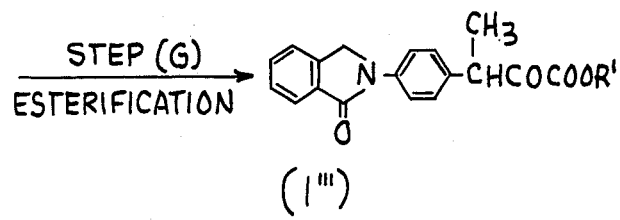

2-OXO-PHENYLBUTANOIC ACID DERIVATIVES

The present invention relates to novel 2-oxo-phenylbutanoic acid derivatives having anti-inflammatory activity and low toxicity, and relates to methods for the production of these derivatives. The present invention also relates to pharmaceutical compositions containing a therapeutically effective amount of at least one of these derivatives and the use of such derivatives and compositions.

Heretofore, it has been known that some of the phenylacetic acid derivatives and phenylpropanoic acid derivatives have anti-inflammatory and analgesic activities, and in fact some of them have been put into a practical use.

However, it has not been reported that such 2-oxo-phenylbutanoic acid derivatives as represented by the following general formula (Z) have anti-inflammatory and analgesic activities, and therefore, none of them has been put into a practical use as an anti-inflammatory agent.

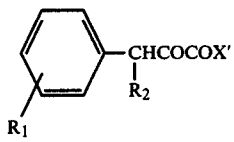

In the formula, X' is amino or hydroxy; $R_1$ is hydrogen or a substituent, and $R_2$ is lower alkyl.

It has now been found that 2-oxo-3-[4-(1-oxo-2-isoindolinyl)phenyl]butanoic acid derivatives of the following general formula (I) have anti-inflammatory and analgesic activities and low toxicity;

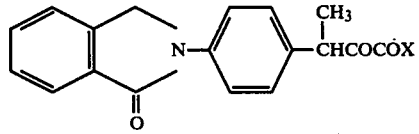

In the formula, X is amino, hydroxy or lower alkoxy.

Thus, the principal object of the present invention is to provide novel compounds (I) which are useful as anti-inflammatory agents, and another object is to provide a pharmaceutical composition containing at least one of the compounds (I). Further, it has been found that from an industrial point of view, the method described hereinafter is advantageous since it is able to produce the compounds (I) by facile operations in a high yield. Thus, further object of this invention is to provide a feasible method for the production of the compounds (I).

Compounds of the general formula (I) are produced by the steps which comprise subjecting N-phenylphthalimidine of the formula (II)

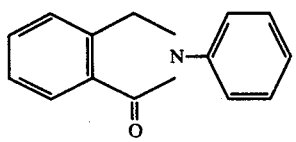

to acetylation to give 4-(1-oxo-2-isoindolinyl) acetophenone of the formula (III)

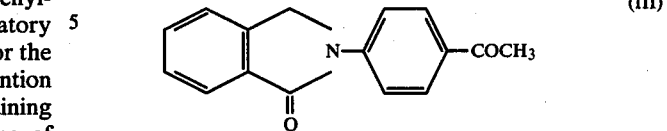

reacting the compound (III) with an ester of cyanoacetic acid to give an ester of 2-cyano-3-[4-(1-oxo-2-isoindolinyl) phenyl]-2-butenoic acid of the general formula (IV)

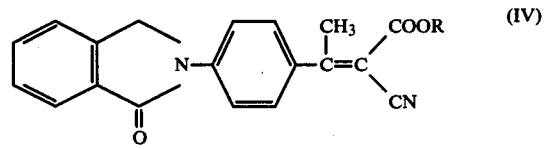

wherein R is lower alkyl, subjecting the compound (IV) to oxidation to give ester of 2-carbamoyl-3-methyl-3-[4-(1-oxo-2-isoindolinyl)phenyl] oxiranecarboxylic acid of the general formula (V)

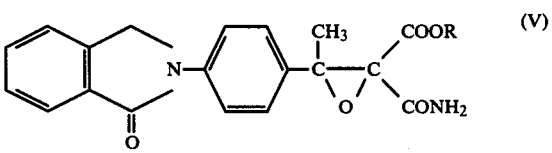

wherein R has the same meaning as defined as above, treating the compound (V) with an alkaline substance to give an alkali metal salt of 2-carbamoyl-3-methyl-3-[4-(1-oxo-2-isoindolinyl)phenyl]oxiranecarboxylic acid of the general formula (VI)

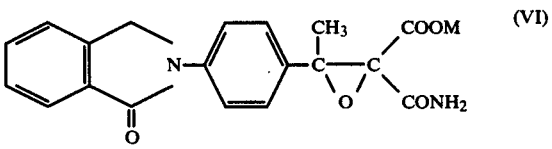

wherein M is alkali metal, and then subjecting the compound (VI) to decarboxylation.

If desired, the thus produced compound may be subjected to hydrolysis, and, if desired, the hydrolysis product may be subjected to esterification.

The lower alkoxy group represented by the symbol X in the general formula (I) may be represented by the formula —OR', wherein R' is lower alkyl. As the lower alkyl group R', there may be, for example, lower alkyl groups having 1 to 4 carbon atoms such as methyl, ethyl, propyl, isopropyl and butyl. The lower alkyl group represented by the symbol R in the general formulae (IV) and (V) may be the same lower alkyl group having 1 to 4 carbon atoms as represented by the symbol R'. The process of this invention is summarized in the FIGURE.

Step (A) is carried out by acetylating Compound (II). Acetylation of Compound (II) under the conditions a Friedel-Crafts Reaction gives selectively Compound (III) in a high yield. N-phenylphthalimidine (II) is reacted with an acetylating agent in the presence of a suitable solvent and Lewis acid to give Compound (III). As the acetylating agent, there may be a reactive derivative of acetic acid such as acetyl halide (e.g. acetyl chloride, acetyl bromide), acetic anhydride. The amount of the acetylating agent is generally 1 to 2 moles per mole of Compound (II). As Lewis acid, there may be any acid which is employable in Friedel-Crafts Reaction. Typical examples of Lewis acid are aluminum chloride, titanium chloride, boron trifluoride, stannic chloride and zinc chloride. Substantially any solvent may be employed provided that it does not disturb the reaction. These may include, for example, methylene chloride, 1,2-dichloroethane, chloroform, carbon disulfide, nitromethane and nitrobenzene. Among them, carbon disulfide and 1,2-dichloroethane are particularly preferable.

The reaction temperature is from −10° C. to 150° C., but the reaction is generally carried out at a temperature of from room temperature to 80° C. The reaction time is usually from about 5 to 72 hours. The produced compound (III) may be isolated and purified by conventional means such as recrystallization with a suitable solvent (e.g. methanol, ethanol, chloroform, benzene, acetic acid), and column-chromatography.

Step (B) is carried out by reacting 4-(1-oxo-2-isoindolinyl)acetophenone (III) with an ester of cyanoacetic acid in the presence of a catalyst such as mixture of benzylamine and acetic acid, and in the presence of a solvent. As the ester of cyanoacetic acid, there may be used, for example, lower alkyl ester of having 1 to 4 carbon atoms such as methyl ester, ethyl ester, propyl ester, isopropyl ester and butyl ester of cyanoacetic acid. The amount of the ester is usually 1 to 2 moles per mole of Compound (III). As the catalyst, a mixture of benzylamine and acetic acid is the most preferable for the reaction of this step, additionally, there may be used a mixture of ammonium acetate and acetic acid; organic acid salts of amine such as piperidinium acetate, piperidinium benzoate; and organic acid salts (e.g. acetate and benzoate) of some amines such as piperidine, morpholine, triethylamine, aniline and diethylamine. As the catalyst, there may be also used amino acid such as glycine and alanine. As the solvent, any solvent may be employable provided that it does not disturb the reaction. These may include benzene, toluene, xylene, chloroform and cyclohexane. It is preferable to carry out the reaction of this step while removing water, which is produced during the reaction, as an azeotropic mixture with a solvent used. The reaction time is usually from 1 to 48 hours. The reaction may be carried out preferably at about temperature of the boiling point of a solvent used. After completion of the reaction, the 2-cyano-3-[4-(1-oxo-2-isoindolinyl)phenyl]-2-butenoic acid derivative of the general formula (IV) so produced may be isolated and purified by conventional means such as recrystallization or column-chromatography. In the reaction of this step Compound (IV) is produced as mixture of its geometrical isomers, however, any isomer and the mixture thereof may be used as a starting compound for the reaction of the next step (C).

Step (C) is carried out by subjecting Compound (IV) to oxidation. The oxidative reaction is usually carried out in the presence of a solvent and an oxidizing agent. As the oxidizing agent, there may be used combinations of (a) hydrogen peroxide and (b) alkali metal salt of tungstic acid, molybdic acid or phosphoric acid (e.g. sodium tungstate, potassium tungstate, sodium phosphate monobasic, sodium phosphate dibasic, sodium phosphate tribasic, sodium molybdate, potassium molybdate); combinations of (1) acetonitrile, (2) hydrogen peroxide and (3) alkali metal hydroxide or alkali metal carbonate (e.g. sodium hydroxide, potassium hydroxide, sodium carbonate, potassium carbonate); and organic peracids such as perbenzoic acid, peracetic acid, perphthalic acid and percamphoric acid. The amount of the oxidizing agent is usually 1 to 20 moles, more preferably 10 moles per mole of Compound (IV). As the solvent, any solvent may be used provided that it does not disturb the reaction, and alcohols such as methanol, ethanol, propanol and butanol are preferable. The reaction temperature is from 0° to 200° C., more preferably, from 20° to 100° C. In the reaction of this step (C), ester of 2-carbamoyl-3-methyl-[4-(1-oxo-2-isoindolinyl)-phenyl]oxiranecarboxylic acid (V) is usually obtained in a form of carboxylate.

Step (D) is carried out by treating Compound (V) with an alkaline substance. More specifically, Step (D) is carried out by subjecting Compound (V) to hydrolysis to give corresponding alkali metal salt of the carboxylic acid, i.e. Compound (VI). The hydrolysis reaction is usually conducted in the presence of hydrolyzing agent and a solvent. As the hydrolyzing agent, there may be used an alkaline substance such as alkali metal hydroxide (e.g. sodium hydroxide, potassium hydroxide) or an alkali metal carbonate (e.g. sodium carbonate, potassium carbonate). As the solvent, there may be used water, alcohols and mixture thereof. Alcohols such as methanol, ethanol and propanol are preferable. The amount of the hydrolyzing agent is usually 1 to 2 moles per mole of Compound (V). The reaction is preferably carried out at a temperature within the range of from 0° to 150° C., more preferably from room temperature to 100° C. The reaction products of Steps (C) and (D) are obtained in the form of mixtures of the stereo isomers of Compound (V) and of Compound (VI) respectively. However any of the isomers of Compound (V) or mixtures thereof, and any of the isomers of Compound (VI) or mixture thereof may be used as a starting compounds for the next steps (D) and (E) respectively. Compounds (IV) to (VI) obtained in Steps (B) to (D) are novel compounds.

Step (E) is carried out by subjecting Compound (VI) to decarboxylation. The decarboxylation reaction is carried out by heating Compound (VI) in the presence of an acid. The reaction temperature is within the range of from 50° to 200° C., more preferably of from 80° to 150° C. As the acid, there may be used an organic acid such as acetic acid, propanoic acid and butanoic acid; and a mineral acid such as hydrochloric acid, hydrobromic acid and sulfuric acid. In the reaction it is not necessary to use a solvent, but as the solvent there may be used mixture of the acid and a solvent such as alcohols (e.g. methanol, ethanol, propanol) and hydrocarbons (e.g. benzene, xylene, toluene). The reaction is preferably carried out in the presence of acetic acid under reflux. The reaction time is from about 30 minutes to 10 hours, more preferably about 4 hours. The reaction of step (E) gives 2-oxo-3-[4-(1-oxo-2-isoindolinyl)-phenyl] butanamide (I′), which is a compound of the general formula (I) wherein X is amino. If desired, Compound (I′) may be converted to Compound (I″), which is a compound of the general formula (I) wherein X is hydroxy, by hydrolysis of the step (F).

Step (F) is carried out by subjecting Compound (I′) to hydrolysis. The hydrolysis reaction is usually carried out in the presence of a solvent and hydrolysis agent. As the hydrolyzing agent there may be employed an alkali metal hydroxide (e.g. sodium hydroxide, potassium hydroxide), an alkali metal carbonate (e.g. sodium carbonate, potassium carbonate), and a mineral acid (e.g. hydrochloric acid, sulfuric acid). As the solvent, any solvent may be used provided that it does not disturb the reaction, and there may be water, alcohols such as methanol, ethanol and propanol, and mixture thereof. The reaction temperature is from 0° to 200° C., more preferably, from room temperature to 100° C. The reaction time is usually from 10 minutes to 5 hours. Referring to Compounds (I') and (I''), which are reaction products of Steps (E) and (F) respectively, there are optical isomers of Compounds (I') and (I'') respectively. After completion of the reactions of Steps (C) to (F), the respective reaction product may be isolated and purified by conventional means such as recrystallization and column-chromatography.

Compound (I'') may be converted to its pharamaceutically acceptable salts such as alkali metal salts (e.g. sodium salts, potassium salts), aluminum salts, calcium salts and tri-lower alkyl amine salt (e.g. triethyl amine salts) by per se conventional means. If desired, Compound (I'') may be converted to Compound (I'''), which is a compound of the general formula (I) wherein X is a lower alkoxy group represented by the formula —OR', wherein R' is lower alkyl, by the esterification of the step (G).

Step (G) is carried out by subjecting Compound (I'') to esterification. The esterification is usually carried out by reacting Compound (I'') with lower aliphatic alcohol in the presence of a solvent by any conventional method.

As the lower aliphatic alcohol, there may be used alcohols corresponding to the lower alkyl group represented by R', and there may be exemplified methanol ethanol, propanol, isopropanol and butanol. As the solvent, an excess amount of the alcohol may be used preferably, but other solvent systems may be used in a form of a mixture with the alcohols. As the other solvent, there may be, for example, benzene, toluene, xylene and chroloform. The reaction temperature is from 0° to 250° C., more preferably, from room temperature to 150° C. The reaction time is from 30 minutes to 5 hours. The esterification is preferably carried out in the presence of a catalyst. As the catalyst, there may be, for example, mineral acid such as hydrochloric acid, sulfuric acid and hydrobromic acid. The amount of the mineral acid is one mole or more per mole of Compound (I'').

According to conventional methods, the esterification may also be carried out by initially converting Compound (I'') with halogenating agent to its acid halide, and then reacting the produced acid halide with the lower aliphatic alcohols described hereinbefore. As the halogenating agent, there may be, for example, thionyl chloride, thionyl bromide, phosphorus oxychloride and phosphorus trichloride. As the solvent, there may be used the same solvents as those to be used in the reaction between Compound (I'') and the lower aliphatic alcohols described hereinbefore. The reaction temperature is within the range of from −20° to 150° C., more preferably, from 0° to 100° C. This esterification is preferably carried out in the presence of organic amines such as pyridine. Any other of the conventional esterification methods may be applied in the esterification of this step (G).

After completion of the esterification the produced compound (I''') may be isolated and purified by conventional means such as recrystallization and column-chromatography. Compound (I'''), exists in the form of optical isomers which may be separated, if desired.

Phenylphthalimidine of the formula (II) [L. Butula, D. Kolbah and I. Butula, Croat. Chem. Acta, 44 (4), 481, (1972),], which is a starting compound of the method of this invention, may be produced according to conventional methods. For example, Compound (II) is preferably produced in a high yield by heating aniline and phthalic anhydride in the absence of a solvent to give N-phenylphthalimide in an almost quantitative yield, and then subjecting the obtained N-phenylphthalimide to reduction with zinc and acetic acid.

Thus produced 2-oxo-3-[4-(1-oxo-2-isoindolinyl)-phenyl]butanoic acid derivative of the general formula (I) and its salt have anti-inflammatory and analgesic activities without undesirable side effects such as gastric difficulties, and are useful as medicine as anti-inflammatory agent and/or analgesic agents. The compound (I) has less toxicity than the known anti-inflammatory agents. Compounds of the general formula (I) are safely applied as an anti-inflammatory and/or analgesic agent.

The test results of anti-inflammatory and analgesic activities, toxicity and appearance of gastic problems of compounds of the general formula (I) are as follows;

EXPERIMENT 1

Anti-Inflammatory Activity (Oral Administration)

Inhibitory effect on carrageenin edema.

(1) Method;

The experiment was carried out according to a method conforming to Van Arman, C. G. et al [The Journal of Pharmacology and Experimental Therapeutics, 150, 328 (1965)]. Each test compound suspended in 0.3% sodium carboxymethyl cellulose (hereinafter abbreviated as CMC-Na) solution was administered orally to 5 male rats in each group (Sprague-Dawley strain) weighing 150 to 200 g in an amount of 1.0 ml per 100 g of body weight of the rat. One hour after the administration of the test compound, 0.1 ml of 1% carrageenin solution in physiological saline was injected subcutaneously into the plantar sarface of the right hind paws of the rats. One hour after injection of carrageenin, the volume of the injected paws was measured hourly for 4 hours. Inhibition percent to carrageenin edema (%)* was calculated in comparison with the volume of paws of rats of a control group, to which only 0.3% CMC-Na solution was orally administered.

Remark
*Inhibition to edema(%) =

$$\frac{\left[\begin{array}{l}\text{Volume of the edema} \\ \text{of the control} \\ \text{group}\end{array} - \begin{array}{l}\text{Volume of the edema} \\ \text{of the test group}\end{array}\right]}{\text{Volume of the edema of the control group}} \times 100$$

(2) Result;
The result is shown in Table 1-(1)

Table 1-(1)

| Test compound | Dose (mg/Kg) | Inhibition to carrageenin edema (%) | |
|---|---|---|---|
| | | 3 hour[a] | 4 hour[a] |
| 2-oxo-3-[4-(1-oxo-2-isoindolinyl)phenyl]butanamide | 12.5 | 29.2 ± 6.4 | 29.3 ± 4.4 |
| | 25 | 29.2 ± 9.0 | 26.6 ± 8.2 |
| | 50 | 35.6 ± 3.9 | 34.1 ± 1.2 |

Table 1-(1)-continued

| Test compound | Dose (mg/Kg) | Inhibition to carrageenin edema (%) 3 hour[a] | 4 hour[a] |
|---|---|---|---|
| | 100 | 51.0 ± 8.6 | 42.8 ± 6.9 |
| Phenylbutazone | 12.5 | 12.0 ± 5.5 | 19.9 ± 3.7 |
| | 25 | 9.6 ± 8.3 | 14.3 ± 4.7 |
| | 50 | 27.1 ± 6.9 | 25.1 ± 5.6 |
| | 100 | 54.3 ± 2.0 | 50.7 ± 6.0 |
| Ibuprofen | 50 | 19.2 ± 22.0 | 23.5 ± 14.2 |
| | 100 | 42.2 ± 0.3 | 33.7 ± 3.1 |
| | 200 | 43.9 ± 1.0 | 37.1 ± 4.7 |

Remark
[a]hour after administration of the test compound.

The value of $ED_{40}$ of the test compounds, which are calculated on the basis of the inhibition percent to edema at 3 hours after administration of the test compound, are as follows;

Table 1-(2)

| Test compound | $ED_{40}$ (mg/Kg) |
|---|---|
| 2-oxo-3-[4-(1-oxo-2-isoindolinyl)phenyl]butanamide | 48 |
| Phenylbutazone | 62 |
| Ibuprofen | 90 |

According to the same method as above, inhibition percent of 2-oxo-3-[4-(1-oxo-2-isoindolinyl)phenyl]-butanoic acid was calculated as follows;

22.5% At dose of 50 mg/Kg and 53.2% at dose of 100 mg/Kg 3 hours after the administration of the test compound respectively.

EXPERIMENT 2

Anti-Inflammatory Activity (Oral Administration)

Inhibition to adjuvant arthritis.

(1) Method;

According to a method conforming to Fujihira et al [Oyo Yakuri, 5, 169, (1971)], liquid paraffin suspension of Mycobacterium butiricum (hereinafter abbreviated as adjuvant) was injected subcutaneously to right hind paws of male rats (Spraque-Dawley strain) weighing 150 to 170 g in an amount of 0.3 mg/0.05 ml/rat. 14 Days after adjuvant injection, the rats, paws of which swelled to a similar degree, were selected and they were separated into groups. From the 15th day after adjuvant injection, each test compound suspended in 0.3% CMC-Na solution was orally administered once a day for 7 days to the 7 rats in each group in the dose shown in the following table 2.

The 16th, 19th and 22nd days after adjuvant injection the volume of left hand paws (i.e. paws not treated with the adjuvant) of the rats and their body weight were measured. Inhibition percent to the arthritis (edema) is calculated according to the same equation as that used in Experiment 1, and the value of $ED_{40}$ is calculated on the basis of the inhibition percent. Then the rats were sacrificed with ether and the weight of their thymus, adrenal glands and spleen was determined.

(2) Result;

The result is shown in Table 2;

Table 2

| Test compound | Dose (mg/Kg) | No. of rats | Increase in body weight (g) | Inhibition to adjuvant arthritis (%) 1st day | 4th day | 7th[b] day | Weight of the organs (mg/100g of body weight) Adrenal glands | Thymus | Spleen |
|---|---|---|---|---|---|---|---|---|---|
| [Control (1)][a] Group of adjuvant arthritis | — | 6 | 41.1 | — | — | — | 8.1 ± 0.3* | 155.5 ± 12.7* | 227.6 ± 11.5* |
| [Control (2)][a] | — | 7 | −4.0 | — | — | — | 18.4 ± 2.8 | 93.0 ± 16.6 | 434.8 ± 22.5 |
| 2-oxo-3-[4-(1-oxo-2-isoindolinyl) phenyl]butanamide | 25 | 7 | 28.4 | 24.0 | 25.1 | 35.2 | 12.5 ± 1.3 | 146.0 ± 7.3* | 441.1 ± 39.6 |
| | 100 | 7 | 40.7 | 32.7 | 34.5 | 45.3 | 11.5 ± 0.7* | 147.2 ± 15.6* | 414.2 ± 28.8 |
| Phenylbutazone | 25 | 7 | 30.9 | 32.2 | 28.8 | 38.3 | 13.2 ± 1.9 | 141.6 ± 12.5* | 441.7 ± 29.9 |
| | 100 | 7 | 31.4 | 34.3 | 37.9 | 51.6 | 12.0 ± 1.0 | 146.2 ± 14.8* | 444.0 ± 39.6 |
| Ibuprofen | 25 | 7 | 26.7 | 25.6 | 15.7 | 32.0 | 13.7 ± 0.9 | 143.3 ± 8.9* | 420.5 ± 34.9 |
| | 100 | 7 | 16.0 | 28.1 | 37.3 | 53.4 | 15.3 ± 1.7 | 127.8 ± 20.7 | 438.0 ± 40.0 |

Remark
*Significant difference from the control (2) ($P<0.05$)
[a]To the rats of the control group (1) [i.e. Control (1)], was administered orally only 0.3% CMC-Na solution without adjuvant injection. To the rats of the control group (2) [i.e. Control (2)] was administered orally only 0.3% CMC-Na solution with adjuvant injection.
[b]days after administration of the test compounds.

EXPERIMENT 3

Analgesic Activity (Oral Administration)

Randall and Selitto method (1) Method;

According to a method conforming to Randall, L. O. and Selitto, J. J. [Archives Internationales de Pharmacodynamie et de Therapie, 111, 409, (1957)], 0.1 ml of 10% Brewer's yeast suspension in physiological saline was injected subcutaneously into the plantar surface of the right hind paws of 5 male rats in each group (Sprague-Dawley strain) weighing 90 to 110 g. 2 Hours after administration of the yeast suspension, each test compound suspended in 0.3% CMC-Na solution was orally administered to the rats in an amount of 1.0 ml per 100 g of body weight of the rat. 30 Minutes, 60 minutes and 120 minutes after administration of the test compounds, threshold values of left and right hind paws of the rats were measured by an electric pressure device made by Daiwa Kinzoku Co., Ltd. (Japan). The change of threshold was obtained by comparing the pain threshold obtained in a group after the yeast injection with that obtained before the yeast injection, in the same group as above. Increasing percent of pain threshold of the test compound was calculated on the basis of the mean changes of threshold of the test group and of that of the control group. Rats of the control group were administered orally only 0.3% CMC-Na solution.

(2) Result;

The result is shown in Table 3-(1)

Table 3-(1)

| Test compound | Dose (mg/Kg) | Increasing percent of pain threshold (%) | | |
|---|---|---|---|---|
| | | 30 | 60 | 120 (minutes)[a] |
| 2-oxo-3-[4-(1-oxo-2-isoindolinyl)phenyl]butanamide | 25 | 15.6 ± 10.3 | 14.1 ± 13.7 | 22.1 ± 18.5 |
| | 50 | 46.9 ± 4.6** | 32.7 ± 5.9 | 48.6 ± 9.0** |
| | 100 | 46.1 ± 6.6** | 32.4 ± 7.0 | 39.0 ± 7.3** |
| | 200 | 57.3 ± 14.8* | 39.7 ± 8.9 | 39.6 ± 6.5** |

Remark
*Significant difference from the control ($P<0.05$)
**Significant difference from the control ($P<0.01$)
[a]minutes after administration of the test compound According to the Litchfield-Wilcoxon method [The Journal of Pharmacology and Experimental Therapeutics, 96, 96, (1949)], $ED_{50}$ value was calculated as follows on the basis of the increasing percent of pain threshold;

Table 3-(2)

| Test compound | $ED_{50}$ (mg/Kg) |
|---|---|
| 2-oxo-3-[4-(1-oxo-2-isoindolinyl)phenyl]butanamide | 100 |
| Phenylbutazone | 250 |
| Ibuprofen | 130 |

Increase in pain threshold value was not observed about the paws of rats that were not injected with the yeast suspension.

EXPERIMENT 4

Analgesic Activity (Oral Administration)

Stretching method (1) Method;

The experiment was carried out according to a method conforming to Koster R. et al [Federation Proceedings 18, 412, (1960)]. Each test compound suspended in 1% gum arabic solution was orally administered to 10 male mice in each group (ddY-strain) weighing 20 to 25 g, that had been fasted for 18 hours prior to the experiment, in an amount of 0.1 ml per 10 g of body weight of the mouse. 30 Minutes after administration of the test compound, 0.6% acetic acid aqueous solution was injected intraperitoneally to the mice in an amount of 0.1 ml per 10 g of body weight of the mouse, and then frequency of writhing syndrome due to acetic acid was counted for 20 minutes. Inhibition percent to the writhing syndrome was calculated in comparison with frequency of writhing syndrome counted on mice of a control group, to which only 1% gum arabic solution was orally administered.

(2) Result;

The result is shown in Table 4.

Table 4.

| Test compound | Dose (mg/Kg) | Inhibition to writhing syndrome (%) |
|---|---|---|
| 2-oxo-3-[4-(1-oxo-2-isoindolinyl)phenyl]butanamide | 100 | 4 |
| | 200 | 33 |
| | 400 | 62 |
| Phenylbutazone | 100 | 10 |
| | 200 | 15 |
| | 400 | 61 |
| Aspirin | 100 | 0 |
| | 200 | 43 |
| | 400 | 70 |

As shown in Table 4, 2-oxo-3-[4-(1-oxo-2-isoindolinyl)phenyl]butanamide shows clear dose-response in dose range of 100 to 400 mg/Kg.

EXPERIMENT 5

Antipyretic activity (oral administration)

(1) Method;

According to a method conforming to Winter, C. A. et al [The Journal of Pharmacology and Experimental Therapeutics 133, 117, (1961)], 20% Brewer's yeast suspension in physiological saline was injected subcutaneously to 5 male rats in each group (Sprague-Dawley strain) weighing 200 to 250 g in an amount of 1.0 ml per 100 g of body weight of the rat. After fasting for 18 hours, each test compound suspended in 1% gum arabic solution was administered orally to the rats in an amount of 1.0 ml per 100 g of body weight. Then, the rectal temperature of the rats was taken. To rats of a control group was administered orally only 1% gum arabic solution.

(2) Result;

Antipyretic activity of 2-oxo-3-[4-(1-oxo-2-isoindolinyl)phenyl]butanamide in dose of 250 mg/Kg showed a drop of 1° C. of febrile body temperature in the rat. With aspirin, a drop of 1° C. of febrile body temperature in rat was observed in dose of 30 mg/Kg.

EXPERIMENT 6

Gross Behaviour (1) (Oral Administration)

(1) Method;

In 1% gum arabic solution was suspended 2-oxo-3-[4-(1-oxo-2-isoindolinyl)phenyl]butanamide at a concentration of 20%. The 20% gum arabic suspension of the compound was administered orally to 5 male mice in each group (ddY-strain) weighing 20 to 25 g. The dosages of the compound were 500, 1000, 2000 and 4000 mg/Kg.

According to a method conforming to Irwin's multi-dimensional observation method [Animal and Clinical Pharmacological Techniques in Drug Evaluation page 36, (1964), Year Book Medical Publishers], gross behaviour of the mice was observed for 4 hours after administration of the compound. To mice of a control group was administered orally only 1% gum arabic solution.

(2) Result;

At any dose level of 500, 1000, 2000 and 4000 mg/Kg, abnormal behaviour such as depression to spontaneous activity, loss of righting reflex, tremor, convulsion, abnormal gait, loss of pinna reflex, loss of corneal reflex and abnormality of respiration were not observed. There was no substantial difference between the gross behaviour of the mice of the test group and that of mice of a control group.

EXPERIMENT 7

Gross Behaviour (2) (Oral Administration)

(1) Method;

In 0.3% CMC-Na solution was suspended 2-oxo-3-[4-(1-oxo-2-isoindolinyl)phenyl]butanamide in at a concentration of 20%. The 20% CMC-Na suspension was administered orally to 3 male rats in each group (Sprague-Dawley strain) weighing 150 to 200 g. The dosage of the compound were 500, 1000, 2000 and 4000 mg/Kg. According to the same manner as that employed in Experiment 6, gross behaviour of the rats was observed for 4 hours after administration of the compound. To rats of a control group was administered orally only 0.3% CMC-Na solution.

(2) Result;

At any does level of 500, 1000, 2000 and 4000 mg/Kg, abnormal behaviour such as depression to spontaneous activity, loss of righting reflex, tremor, convulsion, abnormal gait, loss of pinna reflex, loss of corneal reflex and abnormality of respiration were not observed. There was no substantial difference between the gross behaviour of the rats of test group and that of rats of a control group.

EXPERIMENT 8

Acute Toxicity (1) (Oral Administration)

(1) Method;

In 1% gum arabic solution was suspended 2-oxo-3-[4-(1-oxo-2-isoindolinyl)phenyl]butanamide in at a concentration of 20%. The 20% gum arabic suspension of the compound was administered orally to 10 male mice in each group (ddY-strain) weighing 20 to 25 g. The dosages of the compound were 500, 1000, 2000 and 4000 mg/Kg. After administration of the compound, the number of mice that died during 7 days was observed, and $LD_{50}$ value was calculated on the basis of the mortality.

(2) Result;

At any dose of 500, 1000, 2000 and 4000 mg/Kg, abnormal behaviour, inhibition to increase of body weight and death of the mice of the test group were not observed. Therefore, $LD_{50}$ of this compound in mouse is more than 4000 mg/Kg.

After the observation of 7 days, the mice were sacrificed with ether, and the organs in head, thorax and abdominal cavity of the mice were observed macroscopically. No abnormality was observed.

EXPERIMENT 9

Acute Toxicity (2) (Oral Administration)

(1) Method;

In 0.3% CMC-Na solution was suspended 2-oxo-3-[4-(1-oxo-2-isoindolinyl)phenyl]butanamide in at a concentration of 20%. The 20% CMC-Na suspension was administered orally to 5 male rats in each group (Sprague-Dawley strain) weighing 150 to 200 g. The dosages of the compound were 500, 1000, 2000 and 4000 mg/Kg. After administration of the compound, the number of rats that died during 7 days was observed, and $LD_{50}$ value was calculated on the basis of the mortality.

(2) Result;

At any dose of 500, 1000, 2000 and 4000 mg/Kg, abnormal behaviour, inhibition to increase of body weight and death of the rats of the test group were not observed. Therefore, $LD_{50}$ of the compound in rat is more than 4000 mg/Kg.

After the observation of 7 days, the rats were sacrificed with ether, and the organs in head, thorax and abdominal cavity of the rats were observed macroscopically. No abnormality was observed.

EXPERIMENT 10

Effect on Gastric Mucosa (1) (Oral Administration)

(1) Method;

Each test compound suspended in 1% gum arabic solution was administered orally to 10 male mice in each group (ddY-strain) weighing 20 to 25 g, that had been fasted for 18 hours prior to the experiment, in an amount of 0.1 ml per 10 g of body weight of the mouse. 4 Hours after the administration, the mouse was sacrificed with ether, and its stomach was removed. The stomach was treated with 5% formalin for 3 minutes, and gastric mucosa was observed under a stereoscopic microscope. When gastric lesion in the mucosa was found, the length of each lesion was measured. Degree of gastric damage (i.e. $GD_{50}$)* was calculated on the basis of the length of the lesion of each mouse.

Remark *: $GD_{50}$: The value corresponding to the relative frequency of 50% on the normal probability paper plotted the length of gastric lesions of each mouse.

(2) Result;

The result is shown in Table 5

Table 5

| Test compound | Dose (mg/Kg) | Degree of gastric damage ($GD_{50}$) |
| --- | --- | --- |
| 2-oxo-3-[4-(1-oxo-2-isoindolinyl)phenyl]butanamide | 100 | 1.0 |
|  | 200 | 7.0 |
|  | 400 | 2.5 |
| Phenylbutazone | 100 | 5.2 |
|  | 200 | 10.0 |
|  | 282 | 13.0 |
| Aspirin | 100 | 2.0 |
|  | 200 | 16.1 |
|  | 282 | 18.6 |
|  | 400 | 31.2 |

EXPERIMENT 11

Effect on Gastric Mucosa (2) (Oral Administration)

(1) Method;

Each test compound suspended in 0.3% CMC-Na was administered orally to 5 male rats in each group (Sprague-Dawley strain) weighing 150 to 200 g, that had been fasted for 18 hours prior to the experiment, in an amount of 1.0 ml per 100 g of body weight of the rat. 4 Hours after the administration, the rat was sacrificed with ether, and its stomach was removed. The stomach was treated with 5% formalin for 3 minutes, and gastric mucosa was observed under a stereoscopic microscope. When gastric lesion in the mucosa was found, the number of the lesion in the mucosa was counted.

(2) Result;

The result is shown in Table 6.

Table 6

| Test compound | Dose (mg/Kg) | Mean number of gastric lesion |
| --- | --- | --- |
| 2-oxo-3-[4-(1-oxo-2-isoindolinyl)phenyl]butanamide | 50 | 0 |
|  | 100 | 0 |
|  | 200 | 0.3 |
|  | 400 | 1.6 |
|  | 800 | 0.4 |
| 2-oxo-3-[4-(1-oxo-2-isoindolinyl)phenyl] | 25 | 0 |
|  | 50 | 0 |

Table 6-continued

| Test compound | Dose (mg/Kg) | Mean number of gastric lesion |
|---|---|---|
| butanoic acid | 100 | 1.0 |
| Phenylbutazone | 50 | 0.2 |
| | 100 | 4.2 |
| | 200 | 9.6 |
| Aspirin | 12.5 | 1.0 |
| | 25 | 1.0 |
| | 50 | 5.4 |
| | 100 | 15.0 |

In Experiments 1 to 11, the term "%" means "weight %".

The compound of the general formula (I) has anti-inflammatory and analgesic activities, and is useful as medicine for curing or preventing a disease, which is due to inflammation, of a mammal including mouse, rat and man. The compound of the general formula (I) is used safely as anti-inflammatory agent of the mammals for curing or preventing inflammation of disease such as arthritis, pulpitis, post-operative pain and pain after extraction of tooth. When the compound (I) is used, for example, as an anti-inflammatory agent, one may use the compound (I) without causing substantial side effects, which seem to be due to gastric trouble, such as gastritis, peptic ulcer and bleeding of stomach. When the compound (I) is used as an anti-inflammatory agent, the dose of the compound of the general formula (I) varies depending on severity of disease and kinds of the compound (I) to be used and generally is from about 1 to 100 mg/Kg per day, more preferably 2 to 40 mg/Kg per day for a human adult. The compound (I) is administered orally or parenteraly in solid or liquid administration forms described hereinafter, and oral administration is preferable. Parenteral administration is preferably rectal administration.

The compounds (I) are stable, and among them the compounds (I') and (I'') are more stable. For example, when the compounds (I) are kept at temperature of 50° C., and humidity of 70% for 1 month, no substantial change with respect to their appearances and values of quantitative analysis was observed, and no decomposition product was detected by thin-layer chromatography. Thus compounds (I) are prepared for administration in the form of pharmaceutical compositions according to conventional methods in the field of the art, and it is possible to prepare a pharmaceutical composition which comprises a therapeutically effective amount of at least one compound of the general formula (I) as an active ingredient, i.e. anti-inflammatory composition, in solid administration form (e.g. tablets, granules, powders, capsules, suppository), and liquid administration form (e.g. suspension, emulsion). In that case, as carrier, vehicle, solvent or dispersant, there may be used any of those which are known in the field of art. There may be exemplified water, starch, lactose, crystalline cellulose, magnesium stearate, hydroxypropyl cellulose, mannitol, carboxymethyl cellulose, glycol, ethanol, corn oil, peanut oil, castor oil, cacao butter, isocacao, polyoxyethylene stearate. To these carriers, vehicles, solvents or dispersants, there may be added known supplementary agents such as a stabilizer, preservative, emulsifying agent and buffer solution, and other known pharmaceutically acceptance substances.

By known oxidation procedures, the compounds (I) may be converted to the corresponding phenylacetic acid derivatives, and are useful as intermediates thereof.

For further explanation of the present invention, the following Examples and References are given, wherein the term "part(s)" means "weight part(s)" and the relation between "part" and "volume part" corresponds to that between gram and milliliter.

REFERENCE 1

N-Phenylphthalimide

A mixture of phthalic anhydride (19 g) and aniline (14 g) is heated at 140° to 145° C. for 50 minutes, and to the reaction mixture is added water (50 ml). The resulting powder is collected by filtration, washed with 10% aqueous potassium carbonate solution (50 ml) and water (100 ml), and dried to give colorless powder (28 g, 97%). Recrystallization from acetic acid gives colorless needles.

Melting point: 214° to 215° C.

NMR (d$_6$-DMSO) δ: 7.3 to 8.1 (9H, multiplet, ArH).

REFERENCE 2

N-Phenylphthalimidine

A mixture of N-phenylphthalimide (100 g), zinc powder (147 g) and acetic acid (700 ml) is heated under reflux for 5.5 hours with stirring. After cooling, the mixture is filtered and the insoluble solid is washed with hot acetic acid (100 ml). The combined filtrate and washings are concentrated to give crystal (72 g, 78%). Recrystallization from benzene gives colorless scales.

Melting point: 166° to 167° C.

NMR (CDCl$_3$) δ: 4.8 (2H, singlet, CH$_2$N). 7.1 to 8.1 (9H, multiplet, ArH).

IR $\nu_{max}^{KBr}$ cm$^{-1}$: 1670 (C=O).

EXAMPLE 1

4-(1-oxo-2-isoindolinyl) acetophenone

To a stirred suspension of N-phenylphthalimidine (20.9 g) in carbon disulfide (400 ml), is added acetyl chloride (13.3 g) at room temperature and the mixture is vigorously stirred while aluminum chloride (39.9 g) is added to this mixture in small portions. The whole mixture is refluxed for 4 hours, allowed to stand overnight and further refluxed for 6 hours. After cooling, the organic layer is decanted and the resulting reddish oil is poured into ice cooled 10% hydrochloric acid (300 ml). The percipitated crystals are collected by filtration, washed with water and dried. Recrystallization from ethanol-chloroform gives pale yellow needles (20.6 g, 82%).

Melting point: 243° to 244° C.

Elementary analysis calculated for C$_{16}$H$_{13}$NO$_2$: C, 76.47; H, 5.22; N, 5.57. Found: C, 76.25; H, 5.24; N, 5.61.

NMR (CDCl$_3$) δ: 2.60 (3H, singlet, CH$_3$). 4.93 (2H, singlet, CH$_2$N). 7.5 to 8.2(8H, multiplet, ArH).

Mass spectrum (m/e): 251 (M+).

EXAMPLE 2

Ethyl 2-cyano-3-[4-(1-oxo-2-isoindolinyl)phenyl]-2-butenoate

A mixture of 4-(1-oxo-2-isoindolinyl) acetophenone (17.6 g), ethyl cyanoacetate (15.8 g), benzylamine (7.5 g), acetic acid (50 ml) and toluene (200 ml) is refluxed for 23 hours while removing water produced during the reaction using a Dean and Stark apparatus. The cooled reaction mixture is washed with 10% hydrochloric acid, saturated aqueous sodium chloride solution, saturated aqueous sodium hydrogen carbonate solution and saturated aqueous sodium chloride solution in this order, dried (Na$_2$SO$_4$) and evaporated to give a yellow crystals. Washing with ethyl ether gives crystals (20.6 g, 85%) as a mixture of E-form and Z-form of the object compound (E:Z=5.7:1).

NMR (CDCl$_3$) δ: 1.20 and 1.40 (3H, each triplet, J=7 Hz, CH$_2$CH$_3$). 2.60 and 2.72 (3H, each singlet, CH$_3$). 4.17 and 4.38 (2H, each quartet, J=7 Hz, CH$_2$CH$_3$). 4.90 (2H, singlet, CH$_2$N). 7.2 to 8.3 (8H, multiplet, ArH).

Further recrystallization of the above mixture from ethanol gives the pure E-form compound as pale yellow needles.

Melting point: 163° to 165° C.

Elementary analysis calculated for C$_{21}$H$_{18}$N$_2$O$_3$: C, 72.82; H, 5.24; N, 8.09. Found: C, 72.62; H, 5.23; N, 7.89.

NMR (CDCl$_3$) δ: 1.40 (3H, triplet, J=7 Hz), CH$_2$CH$_3$). 2.72 (3H, singlet, CH$_3$). 4.38 (2H, quartet, J=7 Hz, CH$_2$CH$_3$). 4.90 (2H, singlet, CH$_2$N). 7.2 to 8.3 (8H, multiplet, ArH).

EXAMPLE 3

Ethyl 2-carbamoyl-3-methyl-3-[4-(1-oxo-2-isoindolinyl)-phenyl]oxiranecarboxylate A mixture of ethyl 2-cyano-3-[4-(1-oxo-2-isoindolinyl) phenyl]-2-butenoate (a mixture of E-form and Z-form, 14.0 g), sodium phosphate tribasic (5.0 g), 28% hydrogen peroxide (50 ml) and ethanol is heated at 70° C. for 4 hours. After cooling, the mixture is poured into ice-water. The precipitated colorless crystals are collected by filtration to give crystals as a mixture of E-form and Z-form (14.9 g, 97%). This crystals are recrystallized from ethanol to give the pure E-form compound as colorless needles.

Melting point: 220° C.

Elementary analysis calculated for C$_{21}$H$_{20}$N$_2$O$_5$: C, 66.30; H, 5.30; N, 7.37. Found: C, 66.22; H, 5.35; N, 7.62.

NMR (d$_6$-DMSO) δ: 1.32 (3H, triplet, J=7Hz, CH$_2$CH$_3$). 1.70 (3H, singlet, CH$_3$). 4.37 (2H, quartet, J=7Hz, CH$_2$CH$_3$). 5.03 (2H, singlet, CH$_2$N). 7.2 to 8.2 (8H, multiplet, ArH).

The mother liquor is evaporated and the residue is chromatographed on silica gel with chloroform as an eluent to give a pure Z-form compound. Recrystallization from isopropanol gives colorless needles.

Melting point: 197° to 198° C.

Elementary analysis calculated for C$_{21}$H$_{20}$N$_2$O$_5$: C, 66.30; H, 5.30; N, 7.37. Found: C, 66.06; H, 5.13; N, 7.04.

NMR (d$_6$-DMSO) δ: 0.87 (3H, triplet, J=7Hz, CH$_2$CH$_3$). 1.77 (3H, singlet, CH$_3$). 3.90 (2H, quartet, J=7Hz, CH$_2$CH$_3$). 5.03 (2H, singlet, CH$_2$N). 7.2 to 8.2 (8H, multiplet, ArH).

EXAMPLE 4

Sodium 2-carbamoyl-3-methyl-3-[4-(1-oxo-2-isoindolinyl)phenyl] oxiranecarboxylate To a suspension of ethyl 2-carbamoyl-3-methyl-3-[4-(1-oxo-2-isoindolinyl)phenyl] oxiranecarboxylate (a mixture of E-form and Z-form, 4.0 g) in ethanol, is added ethanolic sodium hydroxide (0.5 g) and the mixture is heated at 70° C. for 2 hours. The precipitated colorless crystals are collected by filtration to give the crystals as a mixture of E-form and Z-form of the object compound (3.9 g, 99%). Under the same conditions as above, E-form of ethyl 2-carbamoyl-3-methyl-3-[4-(1-oxo-2-isoindolinyl) phenyl] oxiranecarboxylate is treated with ethanolic sodium hydroxide to give sodium carboxylate of E-form of the compound.

Melting point: 255° C. (decomposition).

Elementary analysis calculated for C$_{19}$H$_{15}$N$_2$O$_5$Na·0.5H$_2$O: C, 59.53; H, 4.21; N, 7.31. Found: C, 59.17; H, 3.97; N, 7.03.

NMR (d$_6$-DMSO) δ: 1.57 (3H, singlet, CH$_3$). 5.03 (2H, singlet, CH$_2$N). 7.2 to 8.3 (8H, multiplet, ArH).

Similarly, Z-form of ethyl 2-carbamoyl-3-methyl-[4-(1-oxo-2-isoindolinyl)phenyl] oxiranecarboxylate is treated with ethanolic sodium hydroxide to give sodium carboxylate of Z-form of the compound as colorless powder.

Melting point: 212° C. (decomposition).

NMR (d$_6$-DMSO) δ: 1.57 (3H, singlet, CH$_3$). 5.03 (2H, singlet, CH$_2$N). 7.0 to 8.7 (8H, multiplet, ArH).

EXAMPLE 5

2-oxo-3-[4-(1-oxo-2-isoindolinyl)phenyl]butanamide

A mixture of sodium 2-carbamoyl-3-methyl-3-[4-(1-oxo-2-isoindolinyl)phenyl] oxiranecarboxylate (a mixture of E-form and Z-form, 8.0 g) and acetic acid (50 ml) is refluxed for 4 hours, and the reaction mixture is concentrated to give a crystals. Recrystallization from a mixture of acetic acid and ethyl acetate gives the desired product as pale yellow needles (5.5 g, 83%).

Melting point: 220° to 222° C.

Elementary analysis calculated for C$_{18}$H$_{16}$N$_2$O$_3$: C, 70.11; H, 5.23; N, 9.9. Found: C, 69.75; H, 5.08; N, 8.90.

NMR (d$_6$-DMSO) δ: 1.37 (3H, doublet, J=7Hz, CH$_3$). 4.76 (1H, quartet, J=7Hz, CH). 5.03 (2H, singlet, CH$_2$N). 7.1 to 8.2 (8H, multiplet, ArH).

IR $\nu_{max}^{KBR}$ cm$^{-1}$: 1720, 1680, 1660 (C=O).

Mass spectrum (m/e): 308 (M$^+$).

Thin layer chromatography

Rf:0.48 (benzene: chloroform: ethanol=5:5:2).

EXAMPLE 6

2-Oxo-3-[4-(1-oxo-2-isoindolinyl)phenyl]butanoic acid

A mixture of 2-oxo-3-[4-(1-oxo-2-isoindolinyl)phenyl] butanamide (0.30 g) and 10% aqueous sodium hydroxide solution (10 ml) is refluxed for 1 hour. After cooling the reaction mixture is washed with chloroform. The aqueous layer is acidified with diluted hydrochloric acid. The acidified layer is extracted with chloroform and the chloroform layer is washed with water, dried (Na$_2$SO$_4$) and evaporated. The residue is recrystallized from ethyl acetate to give colorless scales (0.23 g, 76%).

Melting point: 216° to 219° C. Elementary analysis calculated for C$_{18}$H$_{15}$NO$_4$: C, 69.89; H, 4.89; N, 4.53. Found: C, 69.70; H, 4.90; N, 4.43.

NMR (d$_6$-DMSO) δ: 1.47 (3H, doublet, J=7Hz, CH$_3$). 4.55 (1H, quartet, J=7Hz, CH). 4.92 (2H, singlet, CH$_2$N). 7.2 to 8.1 (8H, multiplet, ArH).

Mass spectrum (m/e): 309 (M$^+$).

EXAMPLE 7

Ethyl 2-oxo-3-[4-(1-oxo-2-isoindolinyl)phenyl] butanoate

A mixture of 2-oxo-3-[4-(1-oxo-2-isoindolinyl)phenyl] butanoic acid (309 mg) and ethanol (10 ml) saturated with hydrogen chloride gas is refluxed for 5 hours. After removal of the solvent, water is added to the residue and the mixture is extracted with chloroform. The chloroform layer is washed with water, dried (Na$_2$-

SO₄) and evaporated. Recrystallization of the residue from carbon tetrachloride gives colorless needles (306 mg, 91%).

Melting point: 122° to 123° C.

Elementary analysis calculated for $C_{20}H_{19}NO_4$: C, 71.20; H, 5.68; N, 4.15. Found: C, 70.93; H, 5.65; N, 4.15.

NMR (CDCl₃) δ: 1.26 (3H, triplet, J=7Hz, CH₂C$\underline{H}$₃). 1.48 (3H, doublet, J=6Hz, CHC$\underline{H}$₃). 4.27 (2H, quartet, J=7Hz, C$\underline{H}$₂CH₃). 4.56 (1H, quartet, J=6Hz, C$\underline{H}$CH₃). 4.91 (2H, singlet, CH₂N). 7.2 to 8.0 (8H, multiplet, ArH).

IR $\nu_{max}^{KBr}$ cm⁻¹: 1720, 1675 (C↑O).

EXAMPLE 8

2-Oxo-3-[4-(1-oxo-2-isoindolinyl)phenyl] butanoic acid, lactose and starch are mixed according to the following prescription. The mixture is granulated with hydroxypropylcellulose aqueous solution, dried and sieved to give granules.

| Prescription | |
|---|---|
| 2-Oxo-3-[4-(1-oxo-2-isoindolinyl)-phenyl]butanoic acid | 100 weight parts |
| Lactose | 67 weight parts |
| Starch | 30 weight parts |
| Hydroxypropylcellulose | 3 weight parts |
| | 200 weight parts |

EXAMPLE 9

2-Oxo-3-[4-(1-oxo-2-isoindolinyl)phenyl] butanamide, crystalline cellulose, starch and lactose are mixed according to the following prescription. The mixture is granulated with hydroxypropylcellulose aqueous solution, dried and sieved to give granules, and the granules are mixed with magnesium stearate. The resulting granules are compressed with a tableting machine to give tablets.

| Prescription | |
|---|---|
| 2-Oxo-3-[4-(1-oxo-2-isoindolinyl)-phenyl]butanamide | 100 weight parts |
| Crystalline cellulose | 40 weight parts |
| Starch | 30 weight parts |
| Lactose | 27 weight parts |
| Hydroxypropylcellulose | 2 weight parts |
| Magnesium stearate | 1 weight part |
| | 200 weight parts (200 mg/tablet) |

EXAMPLE 10

Ethyl 2-oxo-3-[4-(1-oxo-2-isoindolinyl) phenyl] butanoate, crystalline cellulose, starch and lactose are mixed according to the following prescription. The mixture is granulated with hydroxypropylcellulose aqua solution, dried and sieved to give granules, and the granules are mixed with magnesium stearate. The resulting granules are compressed with a tablet machine to give tablets.

| Prescription | |
|---|---|
| Ethyl 2-oxo-3-[4-(1-oxo-2-isoindolinyl)phenyl]butanoate | 100 weight parts |
| Crystalline cellulose | 40 weight parts |
| Starch | 30 weight parts |
| Lactose | 27 weight parts |
| Hydroxypropylcellulose | 2 weight parts |
| Magnesium stearate | 1 weight part |
| | 200 weight parts (200 mg/tablet) |

EXAMPLE 11

2-Oxo-3-[4-(1-oxo-2-isoindolinyl)phenyl] butanamide, crystalline cellulose, starch, lactose and magnesium stearate are mixed according to the following prescription. The mixture is filled with a filling machine of capsule to give hard capsules.

| Prescription | |
|---|---|
| 2-Oxo-3-[4-(1-oxo-isoindolinyl)phenyl]butanamide | 100 weight parts |
| Crystalline cellulose | 30 weight parts |
| Starch | 28 weight parts |
| Lactose | 40 weight parts |
| Magnesium stearate | 2 weight parts |
| | 200 weight parts (200 mg/capsule) |

EXAMPLE 12

100 weight parts of 2-oxo-3-[4-(1-oxo-2-isoindolinyl)phenyl] butanamide and 1,100 weight parts of Witepsol ® (made by Dynamit Nobel Aktiengesellshaft) are melted at 40° to 70° C. for 20 minutes and the resultant mixture is poured while stirring into a mould 7 mm in bottom diameter and 32 mm in length and allowed to stand to cool. This procedure gives suppositories (1,200 mg/suppository).

What we claim is:

1. A compound of the general formula (I)

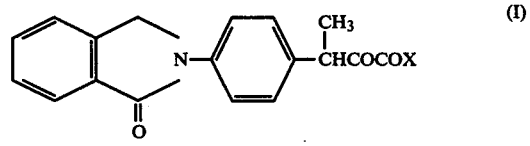

wherein X is amino, hydroxy or lower alkoxy.

2. A compound as claimed in claim 1, wherein X is lower alkoxy.

3. 2-Oxo-3-[4-(1-oxo-2-isoindolinyl)phenyl] butanamide.

4. 2-Oxo-3-[4-(1-oxo-2-isoindolinyl)phenyl] butanoic acid.

5. Ethyl 2-oxo-3-[4-(1-oxo-2-isoindolinyl)phenyl] butanoate.

6. A pharmaceutical composition which comprises an amount which is effective to achieve an anti-inflammatory effect of at least one compound of the general formula (I)

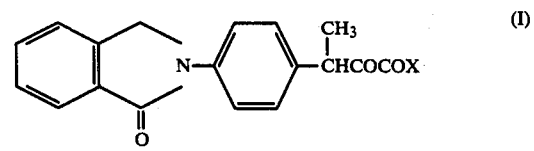

wherein X is amino, hydroxy or lower alkoxy together with a pharmaceutically acceptable carrier.

7. A pharmaceutical composition which comprises an amount which is effective to achieve an analgesic effect of at least one compound of the general formula (I).

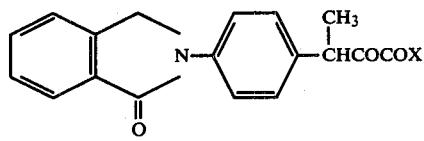
(I)

wherein X is amino, hydroxy or lower alkoxy together with a pharmaceutically acceptable carrier.

8. A pharmaceutical composition which comprises an amount which is effective to achieve an antipyretic effect of the compound 2-oxo-3-[4-(1-oxo-2-isoindolinyl)phenyl] butanamide together with a pharmaceutically acceptable carrier.

9. A method for treating an inflammatory condition in a human which comprises administering an amount which is effective to achieve an anti-inflammatory effect of at least one compound of the general formula (I)

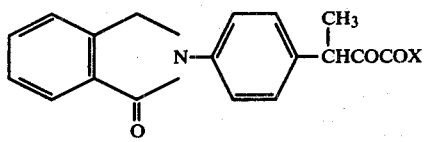
(I)

wherein X is amino, hydroxy or lower alkoxy.

10. A method for achieving an analgesic effect in a human which comprises administering an amount which is effective to achieve such an effect of at least one compound of the general formula (I)

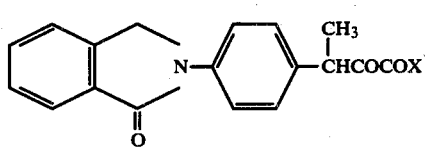
(I)

wherein X is amino, hydroxy or lower alkoxy.

11. A method for treating a pyrectic condition in a human which comprises administering an amount of 2-oxo-3-[4-(1-oxo-2-isoindolinyl)phenyl] butanamide which is effective to achieve an antipyretic effect.

* * * * *